(12) United States Patent
Nikula et al.

(10) Patent No.: US 11,135,323 B2
(45) Date of Patent: Oct. 5, 2021

(54) PRODUCTION OF RE-188/186 PARTICLES

(71) Applicant: ONCOBETA INTERNATIONAL GMBH, Ravensburg (DE)

(72) Inventors: Tuomo Nikula, Ottobrunn (DE); Thomas Wendler, Munich (DE)

(73) Assignee: ONCOBETA INTERNATIONAL GMBH, Ravensburg (DE)

( * ) Notice: Subject to any disclaimer, the term of this patent is extended or adjusted under 35 U.S.C. 154(b) by 58 days.

(21) Appl. No.: 16/340,450

(22) PCT Filed: Oct. 10, 2017

(86) PCT No.: PCT/EP2017/075826
§ 371 (c)(1),
(2) Date: Apr. 9, 2019

(87) PCT Pub. No.: WO2018/069329
PCT Pub. Date: Apr. 19, 2018

(65) Prior Publication Data
US 2019/0290789 A1 Sep. 26, 2019

(30) Foreign Application Priority Data
Oct. 10, 2016 (DE) .................... 10-2016-119-239.2

(51) Int. Cl.
*A61K 51/12* (2006.01)
*A61K 51/02* (2006.01)
*G21G 1/06* (2006.01)
*A61N 5/10* (2006.01)

(52) U.S. Cl.
CPC .......... *A61K 51/1244* (2013.01); *A61K 51/02* (2013.01); *A61K 51/1251* (2013.01); *A61N 5/1029* (2013.01); *G21G 1/06* (2013.01); *A61N 2005/1019* (2013.01)

(58) Field of Classification Search
CPC ...... A61K 9/51; A61K 9/5107; A61K 9/5115; A61K 9/5192; A61K 51/00; A61K 51/02; A61K 51/12; A61K 51/1241; A61K 51/1244; A61K 51/1251; A61K 51/1293
See application file for complete search history.

(56) References Cited

U.S. PATENT DOCUMENTS

| | | |
|---|---|---|
| 2,972,531 A | 2/1961 | Zimmerley et al. |
| 3,260,658 A | 7/1966 | Churchward |
| 5,796,897 A | 8/1998 | Ronan |
| 5,862,193 A | 1/1999 | Jia et al. |
| 6,222,896 B1 | 4/2001 | Jia et al. |
| 6,248,057 B1* | 6/2001 | Mavity ................. A61N 5/1027 600/3 |
| 2004/0197264 A1 | 10/2004 | Schwarz et al. |
| 2007/0031327 A1* | 2/2007 | Luzzi ...................... B82Y 5/00 424/1.11 |
| 2008/0241025 A1 | 10/2008 | Lapi et al. |
| 2013/0172532 A1* | 7/2013 | Yu ........................ A61K 51/081 530/363 |

FOREIGN PATENT DOCUMENTS

| | | |
|---|---|---|
| EP | 2717963 | 4/2014 |
| RU | 2159296 | 11/2000 |
| RU | 2222626 | 1/2004 |
| RU | 2476942 | 2/2013 |
| RU | 2481660 | 5/2013 |
| RU | 2621516 | 6/2017 |

OTHER PUBLICATIONS

Hafeli et al (Hepatic Tumor Radioembolization in a Rat Model Using Radioactive Rhenium (186Re/188Re) Glass Microspheres; Int. J. Radiation Oncology Biol. Phys., vol. 44, No. 1, pp. 189-199, 1999). (Year: 1999).*
Hafeli et al (Stability of biodegradable radioactive rhenium (Re-186 and Re-188) microspheres after neutron-activation; Applied Radiation and Isotopes 54, pp. 869-879, 2001). (Year: 2001).*
Yu et al ([188Re]Rhenium Sulfide Suspension: A Potential Radiopharmaceutical for Tumor Treatment Following Intra-Tumor Injection; Nuclear Medicine & Biology, vol. 26, pp. 573-579, 1999) (Year: 1999).*
Bichakjian et al., "Basal Cell Skin Cancer," NCCN Clinical Practice Guidelines in Oncology, Version 1.2016, NCCN.org.
Eisemann et al., "Non-Melanoma Skin Cancer Incidence and Impact of Skin Cancer Screening on Incidence," The Journal of Investigative Dermatology 134, No. 1, Jan. 2014, 43-50.
Garcia at al., "Basal Cell Carcinoma of the Nasolabial Fold: An Apparently 'Benign' Tumour That Often Needs Complex Surgery," Journal of the European Academy of Dermatology and Venereology: JEADV 20, No. 8, Sep. 2006, 926-930.
Häfeli et al., Hepatic Tumor Radioembolization in a Rat Model Using Radioactive Rhenium (186RE/188RE) Glass MicroSpheres, International Journal of Radiation: Oncology Biology Physics, vol. 44, No. 1, Apr. 1, 1999, 2 pages.
Haves et al., "The Impact of Inoperable Advanced Basal Cell Carcinoma: The Economic, Physical, and Psychological Burden of the Disease," Journal of Drugs in Dermatology: JDD 12, No. 10, Suppl, Oct. 2013, s151-153.
International Search Report for PCT/EP2017/075826 dated Jan. 23, 2018, 12 pages.
Levell et al., "Basal Cell Carcinoma Epidemiology in the UK: The Elephant in the Room," Clinical and Experimental Dermatology 38, No. 4, Jun. 2013, 367-369.

(Continued)

*Primary Examiner* — Micah Paul Young
(74) *Attorney, Agent, or Firm* — Dority & Manning, P.A.

(57) ABSTRACT

Provided is a process of producing activated particles comprising $^{188}$Re-isotopes and/or $^{186}$Re-isotopes by irradiating non-volatile and water-insoluble starting particles comprising a rhenium compound with neutrons. Further provided is a process of producing corresponding non-volatile and water-insoluble starting particles. Further provided are respective starting particles and activated particles, respectively, and a composition comprising a plurality of activated particles. The activated particles, and the composition comprising same are suitable for use in radionuclide therapy, and for cosmetic applications.

21 Claims, 1 Drawing Sheet

(56) References Cited

OTHER PUBLICATIONS

Figure 1:
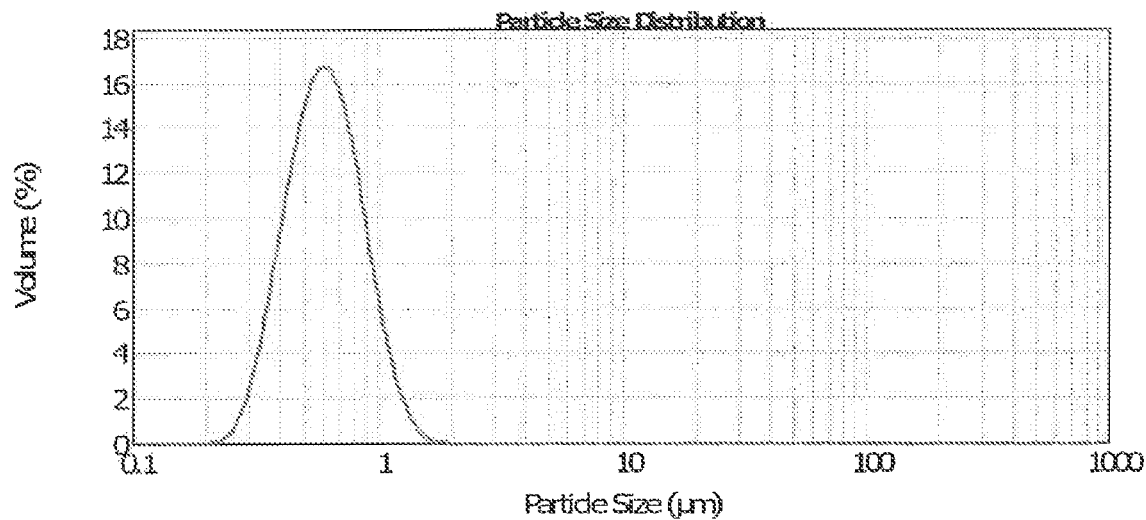

Norval et al., "The Incidence and Body Site of Skin Cancers in the Population Groups of South Africa," Photodermatology, Photoimmunology &Photomedicine 30, No. 5, Oct. 2014, 262-265.
Rogers et al., "Incidence Estimate of Nonmelanoma Skin Cancer in the United States, 2006," Archives of Dermatology 146, No. 3, Mar. 2010, 283-287.
Shipachev, "Some Processing Techniques for Rhenium Isolation and Purification from Refractory Alloys," Chemistry for Sustainable Development 20, 2012, 323-326.
Chile Office Action and Search Report for application 201900951, 9 pages, dated Aug. 31, 2020.
Columbia Office Action for Columbia for application NC2019/0004738, dated Jun. 20, 2020, 7 pages.
Zhang et al., "Preparation of 186Re and 188Re with high specific activity by the Szilard-Chalmers effect," Jan. 28, 2000.
Columbia Office Action for Application No. NC2019/0004738 dated May 15, 2021, 8 pages.
Hafeli et al., "Hepatic Tumor Radioembolization in a rat Model Using Radioactive Rhenium (186RE/188RE) Glass Microspheres," Int. J. Radiation Oncology Biol. Phys., vol. 44, No. 1, pp. 189-1999, 1999, 11 pages.
Russia Office Action for Application No. 2019113502/07(026178), dated Apr. 22, 2021, 7 pages.
"Yttrium-90 and Rhenium-188 Radiopharmaceuticals for Radionuclide Therapy," IAEA, 2015, 320 pages.

* cited by examiner

PRODUCTION OF RE-188/186 PARTICLES

CROSS REFERENCE TO RELATED APPLICATIONS

This application is the U.S. National Stage entry of International Application Number PCT/EP2017/075826 filed under the Patent Cooperation Treaty having a filing date of Oct. 10, 2017, which claims priority to German Patent Application No. 10-2016-119-29.2 having a filing date of Oct. 10, 2016, which are incorporated herein by reference.

TECHNICAL FIELD

The present invention relates to a process for producing and optimizing rhenium-containing, non-volatile and water-insoluble particles under non-radioactive conditions and activating said particles to obtain radioactive rhenium compounds with reduced risk of radioactive tungsten impurities. The activated particles according to the present invention and compositions comprising such particles are useful for medical applications and cosmetic purposes.

BACKGROUND OF THE INVENTION

There are three main types of cells in the top layer of the skin (i.e. the epidermis): squamous cells, basal cells and melanocytes. The most common type of skin cancer is basal cell carcinoma (BCC) usually developing on sun-exposed areas such as the head and neck. Squamous cell carcinoma (SCC) also appears on sun-exposed areas of the body such as the face, ears, neck, lips, cleavage, back, legs, feet, and hands. SCC can also develop in scars or chronic skin soles and the skin of the genital area. Melanomas are much less common than BCC and SCC. Worldwide several millions of people are diagnosed with non-melanoma skin cancer each year [1-4] and thousands of people die.

Of particular relevance are patients bearing these cancers in the head, neck or genital area. Some of these patients are considered very severe "inoperable" cases, currently left only with inadequate or no viable treatment options resulting in high morbidity and often a psychological and economic burden [5, 6]. Also large area or multiple tumors are considered as severe in many cases, as surgery is involves complicated plastic reconstruction with high chances of failure and often not possible at all. Treatment cost for such severe cases can be estimated to range between €10,000 and €120,000 (and more) depending on localization, stage of the disease, need for transplants, complications, co-morbidity, etc. Thus, means for treating such severe cases with an innovative non-invasive curative approach are urgently awaited. The gained knowledge and medical expertise can then also be applied to easier cases, other skin diseases and cosmetic applications.

One strategy for severe cases of cancer is radiation therapy using electron beams or low energy X-rays ("soft" X-rays). However, it is contraindicated for some non-melanoma skin cancers such as verrucous carcinoma (VC) and patients with genetic predisposition to skin cancer and connective tissue diseases. Further, due to the radiation burden, it is not recommended for patients younger than 60 years. The reason for these constraints is the fact that these therapies irradiate not only the tumor, but healthy surrounding and deeper tissue too. The common approach for radiotherapy implies treatment normally over 4-7 weeks in daily doses [7]. The only option for patients that cannot undergo such treatments or where they have failed to work is the use of chemotherapy with significant co-morbidity and only a low rate of response.

In contrast, by using radioactive material with low penetration emissions applied directly to the abnormal skin a very local radiation therapy can be performed allowing for flexibility regarding the lesion extension and site. It has been demonstrated that a synthetic inert resin matrix containing the radioactive material can be effectively applied on the surface of a BCC or SCC. This "paint" dries out within few seconds after application in a flexible film and irradiation can be performed strictly limited to the area affected. After a short time, i.e. such as 45 to 90 minutes, depending on the desired irradiation dose and penetration depth. A protective foil placed between skin and the paint is used to avoid the skin to be in contact with the radioactive material and can be removed together with the hardened resin after the treatment.

Naturally occurring rhenium has only one stable isotope, $^{185}$Re, which occurs in minority abundance of 37%. The major natural isotope is $^{187}$Re (63%), which is unstable but has a long half-life (i.e. 41.2*10$^9$ years). $^{186}$Re and $^{188}$Re are artificial isotopes that are used, for example, as radioactive tracer and for other applications in nuclear medicine.

The beta-emitter $^{188}$Re has proved to be an ideal choice as a radioactive source for radionuclide therapy. $^{188}$Re has a half-life of about 17 hours and the average penetration of its irradiation into the skin is about 2-3 mm (92% of its deposited dose is below 3 mm depth). This is sufficient to treat most BCC and SCC without damaging lower layers of the skin and underlying tissue. Besides beta-emission, $^{188}$Re also emits to about 15% gamma-irradiation of 155 keV which enables the use of standard nuclear medicine technologies to detect potential contamination.

The beta-emitter $^{186}$Re as well is an excellent choice as a radioactive source for radionuclide therapy. $^{186}$Re has a half-life of about 89.25 hours and the average penetration of its irradiation into the skin is about 1-1.2 mm (94% of its deposited dose is below 1 mm depth). This is sufficient to treat thin BCC and SCC or BCC and SCC located in areas with thin skin (e.g. eye lids, ears) or mucous membranes (lips, genitals) without damaging lower layers of the underlying tissue.

The suitability of $^{188}$Re as a radioactive source has been demonstrated at an Italian study with over 750 patients, wherein a large variety of BCC and SCC forms, i.e. tumors of very large size to relapsing or recurrent forms and multifocal lesions, have been treated successfully in 99% of over 2,000 lesions.

According to the currently used method, $^{188}$Re is generated using $^{188}$W/$^{188}$Re generators. Clinics which are able to offer a treatment with $^{188}$Re have their own $^{188}$W/$^{188}$Re generators, and accordingly $^{188}$Re is generated at the location where it is subsequently used in therapy. The current method therefore provides short paths, which is particularly advantageous in view of the short half-life of about 17 hours of $^{188}$Re. The possibility to generate $^{188}$Re on-site therefore has been considered as an essential practical requirement for the use of $^{188}$Re in radionuclide therapy.

However, the current method of producing the radioactive source has certain disadvantages. For example, when eluting $^{188}$Re from the generator, the solution always contains $^{188}$W impurities. Due to the long half-life of $^{188}$W (about 70 days) such impurities are of significant concern when it comes to the disposal of radioactive waste. The amount of $^{188}$W impurities varies from generator to generator and amounts increase over the life time of the generator. Additionally, mishandling of the generator might cause sudden increase of $^{188}$W impurities (i.e. $^{188}$W passes to the $^{188}$Re solution). $^{188}$W impurities can be detected after several half-lives of $^{188}$Re on the basis of the longer half-life. However, this leads to a loss of already limited amounts of radioactivity during the time of waiting prior to the measurement.

Furthermore, the availability of $^{188}$Re in sufficient radioactive concentration is a considerable challenge. Generating the parent $^{188}$W radionuclide (being the starting isotope in $^{188}$W/$^{188}$Re generators decaying to $^{188}$Re) requires a double neutron capture route. This impedes the availability of $^{188}$Re, since $^{188}$W at adequate specific activity can be prepared only in as little as three high flux reactors operating in the World.

Further, according to the currently used method, $^{188}$W can be detected only afterwards with potentially serious consequences regarding radioactive waste management. Further, reactions to transfer the eluted $^{188}$Re into stable, non-volatile compounds require specific laboratory facilities guaranteeing for radiation safety. Also, if a production fails, the production line needs to be cleaned from residual radioactivity. Due to radiation protection, this can only be done at the earliest two days after production. Finally, using generators also constrains the maximum radioactivity per volume unit that can be eluted, which may result in too low radioactive yield for practical means.

Due to the limited availability and considerable production costs, the feasibility of quality analysis of the final product is limited. However, parameters such as the size of the obtained radioactive particles and their size distribution are of particular relevance when using the radioactive source in therapeutic and cosmetic applications.

What is needed, therefore, is a process for producing a radioactive source of desired radioactive properties that is easily available, cost efficient in production and manageable in terms of radiation protection. This need is met by the present invention.

LIST OF FIGURES

FIG. 1 shows a distribution of particle sizes for $Re_2S_7$ obtained by a process according to the invention. There is a single peak with a narrow spread. The average size may be adjusted as needed.

Figure 2:
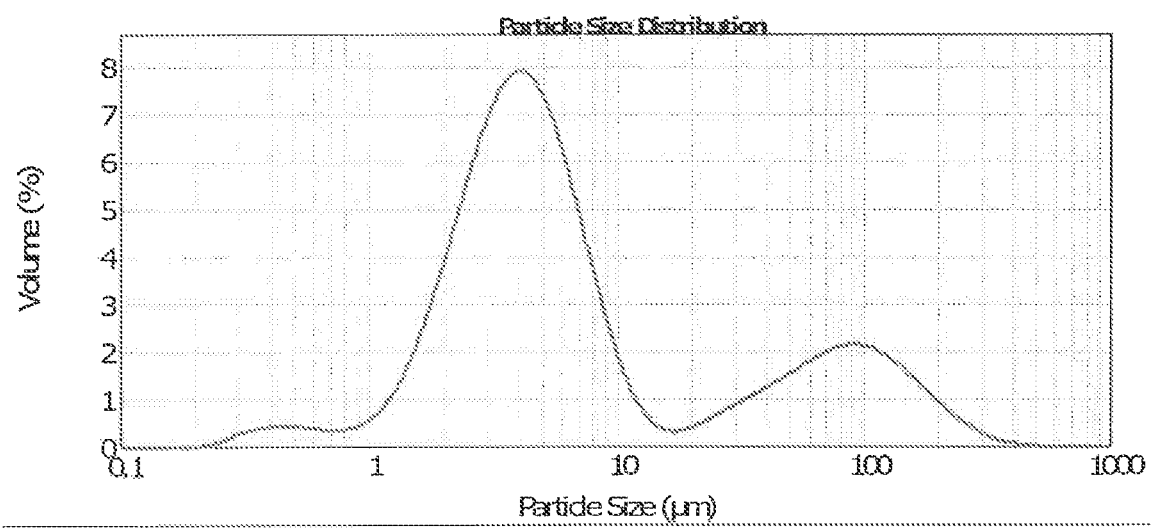

FIG. 2 shows a distribution of particle sizes for $Re_2S_7$ obtained by the process of the comparative example, i.e. according to the conservative method. At least three peaks can be seen, all of them being more than an order of magnitude away. The peaks are also broader than in FIG. 1.

DEFINITIONS

Before the present invention is described in detail below, it is to be understood that this invention is not limited to the particular processes, protocols and particles described herein as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art.

In the following, some definitions of terms frequently used in this specification are provided.

In the event of a conflict between common definitions or teachings and definitions or teachings recited in the present specification, the text of the present specification takes precedence.

In the context of the present invention, the term "particles" refers to particulate matter such as atoms, clusters of atoms or molecules of single or multiple elements. In general, there is no restriction regarding the quantity of matter forming a particle.

The term "starting particles" is used herein to refer to particles prior to activation according to the present invention. Hence, the term starting particles as used in context of the present invention refers to non-radioactive particles. A preferred size range of the starting particles is about 1 nanometer to 100 micrometers, such as from 10 nanometers to 20 micrometers, from 20 nanometers to 10 micrometers, from 50 nanometers to 5 micrometers, or from 100 nanometers to 1 micrometer. The starting particles according to the present invention are non-volatile and water-insoluble. In this context, the term "non-volatile" refers to particles having a low tendency to vaporize. This means, the starting particles may have a vapor pressure below 100 Pa at 20° C. Further in this respect, the term "water-insoluble" is used herein to refer to particles being poorly soluble in water, i.e. having a solubility in water below 0.1 g per 100 g of water at 20° C. and atmospheric pressure.

The term "activated particles" as used herein refers to particles forming upon activation of the starting particles. In this respect, "activation" is used to refer to a neutron capture event in a neutron-source such as a nuclear reactor. In this context, the term "neutron capture" refers to a nuclear reaction in which an atomic nucleus collides with a neutron, merges and forms a heavier nucleus, i.e. a different isotope. With respect to the present invention, the term "isotope" refers to variants of a particular chemical element which differ in neutron number, but have the same proton number. Particular examples of isotopes referred to herein are $^{185}$Re, $^{186}$Re, $^{187}$Re, and $^{188}$Re. Further, in this respect, the term "irradiating" is used herein to refer to the process by which the starting particles according to the invention are exposed to a neutron flux. Depending on the irradiation facility, the thermal neutron flux density may vary. Neutrons can be provided by fission of uranium which initially supplies fast, i.e. high-energy neutrons. To obtain lower-energy thermal neutrons, the neutrons are slowed down by collision with the surrounding water. In this context, the term "thermal neutrons" refers to free neutrons with a kinetic energy smaller than 0.6 eV, i.e. about 0.025 eV.

The term "rhenium compound" refers to a compound comprising rhenium. The specific composition of these compounds is not particularly limited as long as the particles comprising the rhenium compound are non-volatile and water-insoluble. For example, the rhenium compounds according to the present invention may be rhenium sulfide, rhenium oxide or combinations thereof. In particular, the rhenium compound may be selected from a dirhenium heptasulfide, rhenium disulfide, a rhenium dioxide, rhenium trioxide, dirhenium heptaoxide, and combinations thereof. For example, the rhenium compound of the invention may comprise or essentially consist of $Re_2S_7$, i.e. $^{187}Re_2S_7$.

The term "rhenium solution" is used herein to refer to a fluid comprising rhenium, i.e. a solution such as an aqueous solution or a melt. A rhenium solution according to the invention may be a perrhenate solution. In this respect, the term "perrhenate" refers to the metaperrhenate ($ReO_4^-$) anion. A perrhenate solution can be obtained by converting metallic rhenium. In this context, the term "metallic rhenium" refers to elemental rhenium. Metallic rhenium can be converted to perrhenate solution by one of several ways.

Metallic rhenium readily dissolves in nitric acid by a reaction as depicted in Formula (I).

$$3Re+7HNO_3->3HReO_4+7NO+2H_2O \qquad \text{(Formula I)}$$

Further, metallic rhenium is slowly soluble in sulfuric acid. In this context, it is of note that according to the insight of the inventor, all modes of acid attack can lead to undesirable losses of volatile perrhenic acid ($HReO_4$).

Another possibility of converting metallic rhenium is fusion with NaOH or NaOH+$NaNO_3$ or $Na_2CO_3$. Metallic rhenium is stable below 1,000° C. and atmospheric pressure. When fused with NaOH it forms a yellow melt from which $Na_2ReO_4$ may be obtained. Alkali perrhenates can be melted without decomposition.

Further, rhenium material can be converted to soluble perrhenate by fusion with $Na_2O_2$. Fusion with $Na_2CO_3$ or with $Na_2CO_3$+$NaNO_3$ is also possible and has the advantage that platinum crucibles can be used. $NaNO_3$ may be added if a stronger oxidizing environment is necessary. Further, sodium can also be replaced with potassium in the above mentioned compounds. However, it is the insight of the present inventor that there is a risk that some alkali metal residues will end up on the particles according to the invention, which may be activated during the neutron activation process. Stable $^{23}Na$ and $^{39}K/^{41}K$ atoms can get activated to form undesirable $^{24}Na$ (strong gamma-emitters with a non-significant beta-emission) and $^{40}K/^{42}K$ (both beta-emitters with $^{42}K$ being a strong gamma-emitter). Further, metallic rhenium can be converted to soluble perrhenate by reaction with hydrogen peroxide ($H_2O_2$) under alkaline conditions (i.e. at a pH above 7). Conversion may be performed in an aqueous mixture of NaOH or $NH_4OH$ and $H_2O_2$.

The term "precipitating agent" as used herein refers to a compound used for the creation of a solid from a solution during a chemical reaction. According to the present invention, dissolved rhenium (such as in form of perrhenate) can be precipitated from its solution using a suitable precipitating agent. In this respect, the perrhenate solution may be reconditioned and sulfide precipitation may be started. For example, the source of sulfur may be dihydrogen sulfide ($H_2S$) which may be gassed into the solution or may be produced in the solution from sources such as thioacetamide ($CH_3CSNH_2$) or similar compounds. In particular, the precipitating agent of the invention for precipitating dissolved rhenium may be sulfide in form of thioacetamide. $CH_3CSNH_2$ is hydrolyzed under strong acid conditions (i.e. at a pH below 2):

$$CH_3CSNH_2+2H_2O->CH_3COOH+H_2S+NH_3 \qquad \text{(Formula II)}$$

The perrhenate anion $ReO_4^-$ reacts with $H_2S$ to generate $Re_2S_7$.

$$7H_2S+2ReO_4^-+2H_3O+->Re_2S_7+8H_2O \qquad \text{(Formula III)}$$

The term "average particle size" as used in context of the present invention refers to the central value of the particle size distribution of a certain sample. The size can be determined by several physical parameters known to the person skilled in the art, such as the mesh size of a sieve, the scattered light, the settling rate in a sedimentometer or by analysis of a microscopic image. Assuming a symmetric particle size distribution, the central value is representing not only the mean particle size, but also the median and the mode of the distribution. As it is known to the skilled reader, particle dimensions can be expressed by different parameters (e.g. diameter, aspect, surface, or volume). Consequently, there are also multiple definitions for the mean depending on the basis of the distribution calculation. For example, laser diffraction results are reported on a volume basis, so the volume mean can be used to define the central point of a particle size distribution, i.e. the average particle size. The volume mean can be calculated as shown in Formula (IV)

$$D43=\Sigma D^4/\Sigma D^3 \qquad \text{(Formula IV)}$$

The calculation can be interpreted by thinking of a histogram table showing the upper and lower limits of n size channels along with the percent within this channel. The D value for each channel is the geometric mean, i.e. the square root of upper×lower diameters. For the numerator of Formula (IV) the geometric mean of each channel to the fourth power×the percent in that channel is summed over all channels. For the denominator the geometric D to the third power×the percent in that channel is summed over all channels.

In contrast, median values are defined as the value where half of the population resides above this point, and half resides below this point. Assuming spherical particles, the volume-basis median value D50 is the size in micrometers that splits the particle size distribution with half above and half below this diameter.

The mode is the peak of the frequency distribution, i.e. the particle size (or size range) most commonly found in the distribution.

The average particle size of the particles according to the present invention may correspond to a D50 value of from 1 nanometer to 100 micrometers, such as a diameter of from 10 nanometers to 20 micrometers, from 20 nanometers to 10 micrometers, from 50 nanometers to 5 micrometers, or from 100 nanometers to 1 micrometer.

As known to the skilled person in the art, the term "particle size distribution" as used herein refers to a mathematical function that defines the relative amount of particles present according to size. In addition to the location of the peak value(s) of this function, the width or breadth of the distribution is of particular relevance. A common approach to define the distribution width is to determine the D10, D50, and D90 values on the x-axis of the graph. While the D50 value, i.e. the median, corresponds to the diameter where half of the population lies below this value, the D90 and D10 values indicate the diameter below which 90% and 10% of the population lies, respectively.

According to the present invention, the particle size distribution D90, i.e. the diameter below which 90% of the particle sizes are located, may be in the range of 10% to 1.000% of the average particle size. That is to say that the D90 may be in the range of 0.1×D50 and 10×D50. Preferably, the particle size distribution D90 is in the range of 25% to 400% of the average particle size, i.e. in the range of 0.25×D50 and 4×D50. More preferably, the particle size distribution D90 is in the range of 50% to 200% of the average particle size, i.e. in the range of 0.5×D50 and 2×D50.

The term "homogeneously dispersed" as used herein refers to an emulsion in which the particles according to the present invention are in a continuous phase with a matrix component. In this context, the term "matrix or matrix component" refers to a carrier or a component of a carrier which is used as an auxiliary compound for taking up the activated particles according to the invention. In this respect, the term "resinous matrix" is used to refer to a semi-fluid resin.

The term "% or percentage" as used herein refers to wt % or weight percentage unless otherwise indicated.

DETAILED DESCRIPTION OF THE INVENTION

In the following paragraphs different aspects of the invention are defined in more detail. These aspects are listed as specific embodiments, however, it should be understood that they may be combined in any manner and in any number to create additional embodiments. The variously described examples and preferred embodiments should not be construed to limit the present invention to only the explicitly described embodiments. Each aspect defined may be combined with any other aspect or aspects unless the context indicates otherwise. In particular, any feature indicated as being exemplary, preferred or advantageous may be combined with any other feature or features indicated as being exemplary, preferred or advantageous.

In the work leading to the present invention, it was surprisingly shown that by a process for producing non-volatile and water-insoluble starting particles and activating such particles a radioactive source of desired properties can be generated.

According to a first aspect of the present invention, there is provided a process of producing activated particles comprising $^{188}$Re and/or $^{186}$Re. The process comprises providing non-volatile and water-insoluble starting particles comprising a rhenium compound, and irradiating the particles with neutrons. During the irradiation, at least part of the $^{187}$Re atoms undergo a neutron capture to form $^{188}$Re and/or at least part of the $^{185}$Re atoms undergo a neutron capture to form $^{186}$Re, thereby forming said activated particles.

It is an insight of the inventors that the method of the present invention allows for the preparation of non-volatile and water-insoluble stalling particles comprising a rhenium compound under non-radioactive conditions. Hence, compared to the conventional method radioactive contamination due to volatile or water-soluble compounds can be diminished. Additionally, the provided starting material can even be stored in-house without the need of radiation safety regulations. Only upon irradiation of the provided starting particles activation is accomplished leading to the radioactive source according to the invention.

In a preferred embodiment of the first aspect, the step of providing said starting particles comprises providing a rhenium solution, optionally, mixing the rhenium solution with at least one additive, reacting the rhenium solution with a precipitating agent, thereby forming said rhenium compound, and precipitating said rhenium compound. The step further comprises isolating particles comprising the precipitated rhenium compound, and optionally may comprise washing and/or filtering and/or drying said particles.

The term "isolating" as used in this context refers to separating the obtained particles. Upon precipitating the rhenium compound, the particles comprising the precipitated rhenium compound may be isolated, for example, by centrifugation. The obtained pellet may then be subjected to a washing step, for example by re-suspension in an aqueous, saline or organic solution, and repeated centrifugation. Also, the term "filtering" as used herein refers to a separation method. For example, the isolated particles may be separated according to size using the sieving effect of a membrane with an appropriate mesh size. Further, the term "drying" as used in this context refers to a step of removing any liquid supernatant of the obtained precipitate.

In a related embodiment, the step of providing a rhenium solution comprises providing metallic rhenium, and reacting the metallic rhenium, thereby obtaining a perrhenate solution.

For example, the step of providing the starting particles may comprise dissolving metallic rhenium in nitric acid, thereby obtaining perrhenic acid. In another embodiment, the step of providing the starting particles comprises converting metallic rhenium by fusion with one of NaOH, NaOH+NaNO$_3$, Na$_2$CO$_3$, Na$_2$CO$_3$+NaNO$_3$, Na$_2$O$_2$, KOH, KOH+KNO$_3$, K$_2$CO$_3$, K$_2$CO$_3$+KNO$_3$, K$_2$O$_2$, thereby obtaining alkali perrhenate.

In a particularly preferred embodiment, the step of providing the starting particles comprises reacting metallic rhenium using peroxide in alkaline conditions, thereby obtaining a perrhenate solution. The exact nature of the peroxide is not particularly restricted, and as a typical example, hydrogen peroxide may be utilized.

Optionally, the step of providing said starting particles may comprise mixing the rhenium solution with one or more additives. In particular, the additive may be selected from polyvinylpyrrolidone (PVP), polyethylene glycol (PEG) and combinations thereof.

According to an insight of the inventors, the size of the provided starting particles can be adjusted by adding certain components. For example, the inventors have observed that adding PVP and/or PEG helps to control the growth of crystals and hinders the growth of bigger crystals in favor of smaller ones. Thus, the distribution of the particle sizes can be unitized depending on the amount of additive mixed with the rhenium solution.

For instance, the provided rhenium solution may be mixed with 1 to 50 wt % PVP or PEG, based on the weight of rhenium. In other words, per 1 mg of the rhenium compound in the rhenium solution 0.01 to 0.5 mg PVP may be added, such as 0.05 to 0.3 mg PVP.

According to another embodiment, the step of providing the starting particles further comprises determining the composition of the starting particles and/or the particle size distribution of the starting particles and/or the moisture content of the starting particles.

In this context, the term "composition of starting particles" refers to the chemical composite of the particles such as the composition of rhenium compounds or the content of impurities. Particles size distributions are determined by methods well known in the art including laser diffraction, dynamic light scattering and image analysis. Further, the term "moisture content" as used herein refers to the quantity of aqueous solution contained in a material, such as the isolated particles. Typical moisture contents of the starting particles are within a range of 0.1-5 wt %, based on the weight of the particles.

It is a particular advantage of the present invention that it enables an uncomplicated determination of quality parameters of the starting particles. The starting particles are not radioactive and thus the particle size, particle composition and the nature and amount of impurities can be easily controlled. In particular, as regards potential impurities, the present invention allows to analyze the starting particles for the presence and amount of elements which might form during activation an isotope having an undesired half-life or emission spectrum. Further, if necessary, an undesirable charge may be disposed without logistic problems in terms of radioactive waste and thus with little loss of financial resources. In contrast, when employing the conservative method, the amount of produced particles is relatively small and their radioactivity is high. Therefore, parameters such as the size and composition of the produced particles, and the nature and amount of impurities cannot be determined routinely. Hence, the present invention provides unexpected advantages in terms of quality analysis and therefore allows to obtain particles with desired properties.

According to a particular embodiment of the first aspect, rhenium having an isotope distribution other than the natural isotope distribution may be used for preparing the starting particles.

For example, rhenium enriched in $^{187}$Re may be used as a starting material. Rhenium enriched in $^{187}$Re can be purchased for instance from Traces Sciences International Corp., Canada. The enrichment is 99.6% (i.e. comprising about 0.4% of $^{185}$Re). When using rhenium enriched in $^{187}$Re as a starting material, activation of the starting particles will result in the production of $^{188}$Re atoms. According to such embodiment, for example at least 65% of the rhenium atoms in the particles may be $^{187}$Re and $^{188}$Re. For example, at least 80%, preferably at least 90%, more preferably at least 95% and even more preferably at least 99%, such as about 99.6% of the rhenium atoms in the particles may be $^{187}$Re and $^{188}$Re.

Vice versa, rhenium enriched in $^{185}$Re as well might be used as a starting material. When using rhenium enriched in $^{185}$Re as a starting material, activation of the starting particles will result in the production of $^{186}$Re atoms. According to such embodiment, for example at least 40%, in particular at least 60%, such as at least 80% of the rhenium atoms in the particles are $^{185}$Re and $^{186}$Re.

The inventors have found that the risk of fluctuations in supply of radioactive material can be reduced by the present invention. Converting at least part of the $^{187}$Re atoms to $^{188}$Re atoms and/or at least part of the $^{185}$Re atoms to $^{186}$Re atoms each requires only one neutron capture event. Hence, irradiation can be performed with almost all research reactors and at only short irradiation times. Furthermore, short irradiation times mitigate the risk of activating atoms to form a long-lived isotope. Today, there are about 30 of such reactors only in Europe. In contrast, for the conventional method $^{188}$Re needs to be provided by elution from $^{188}$W/$^{188}$Re generators. However, the provision of $^{188}$W/$^{188}$Re generators requires to convert $^{186}$W to $^{188}$W for which two neutron capture reactions are needed. There are currently only three nuclear reactors worldwide which can produce suitable amounts of $^{188}$W (i.e. reactors in Grenoble, FR, Oak Ridge, US and Dimitrograd, RU). Therefore, the supply of $^{188}$W is limited and the price is high. If a generator production fails, new $^{188}$W may only available after 3 to 6 months. Hence, the present invention provides for a cost efficient way of obtaining desired particles.

According to another embodiment of the first aspect, the weight percentage of the rhenium compound in the particles is at least 60%, preferably at least 70%, more preferably at least 75%, for example at least 80%. Further, the weight percentage of the rhenium compound in the particles can be at least 91%, 92%, 93%, 94%, 95%, 96%, 97%, 98%, 99%, 99.9% or more.

The rhenium compound may be selected for example from a rhenium sulfide, a rhenium oxide, and combinations thereof. In particular, the rhenium compound may be selected from dirhenium heptasulfide, rhenium disulfide, rhenium dioxide, rhenium trioxide, dirhenium heptaoxide, and combinations thereof. In particular the particles may comprise dirhenium heptasulfide in an amount of at least 50 wt %, optionally in combination with other rhenium compounds.

In a preferred embodiment of the first aspect, the particles have a unimodal particle size distribution. In this context, the term "unimodal" as used herein refers to a particle size distribution possessing a unique mode only, i.e. one size range in which substantially all of the cumulative distribution of the particles is located. For example, FIG. 1 depicts a unimodal particle size distribution.

Typically, the particles have an average particle size in the range of from 1 nanometer to 100 micrometers. For example, the particles have an average particle size in the range of from 10 nanometers to 20 micrometers, from 20 nanometers to 10 micrometers, from 50 nm to 5 micrometers or from 100 nanometers to 1 micrometer.

Typically, the particles have a particle size distribution D90 in the range of 10% to 1,000% of the average particle size. In other words, 90% of the particles typically fall within one order of magnitude below and one order of magnitude above the average size of the particles. Preferably, 95% or even 99% or more of the particles fall within the range of 10 to 1.000% of the average particle size. Further, at least 90% of the particles optionally fall within the range of 25 to 400% of the average particle size, such as within the range of 50 to 200% of the average particle size.

The starting particles are typically irradiated with thermal neutrons. For example, the starting particles may be activated at capsule irradiation with a thermal neutron flux density of about $10^{14}$ neutrons/cm$^2$/s.

According to a particular embodiment, the process of the first aspect further comprises mixing the activated particles with a matrix component. In this context, it is particularly preferable when the activated particles are homogeneously dispersed in the matrix component.

The matrix component is not particularly limited, and any matrix components which are able to form a matrix upon drying, in particular a water-insoluble matrix, may be used. For example, the matrix component may be a resinous matrix, preferably a water-based resinous matrix. For example, a water-based paint might be employed as matrix component, for example an acrylic paint.

In particular where the matrix component is a paint, the matrix component may comprise a particulate filler. For example, the particulate filler may comprise one or more of at least one oxide, sulfide, carbonate, and in particular the filler may comprise $TiO_2$, $Al_2O_3$, $SiO_2$, $Fe_2O_3$, or any combination thereof.

In an embodiment, the average particle size of the particles is at most 1,000% of the average particle size of the particulate filler. For example, the average particle size of the particles may be at most 500% or at most 250% of the average particle size of the particulate filler. Vice versa, the average particle size of the particles may be at least 1%, at least 10% or at least 25% of the average particle size of the particulate filler. It is an insight of the inventors that, when a matrix containing particulate filler is used, the size of the activated particles and the size of the particulate filler advantageously are within similar size ranges (i.e. about 100%) in order achieve a homogenous dispersion of the activated particles within the matrix.

According to a second aspect, the present invention provides a process of producing non-volatile and water-insoluble starting particles comprising a rhenium compound, which particles have an average particle size of from 1 nanometer to 100 micrometers. The process comprises providing a rhenium solution, optionally, mixing the rhenium solution with at least one additive, reacting the rhenium solution with a precipitating agent, thereby forming said rhenium compound, and precipitating said rhenium compound. The step further comprises isolating particles comprising the precipitated rhenium compound, and optionally may comprise washing and/or filtering and/or drying said particles.

Further details of the process according to the second aspect of the present invention are as discussed above in the context of the process according to the first aspect of the present invention.

Further, as also already discussed above in the context of the process according to the first aspect of the present invention, rhenium enriched in $^{187}$Re or rhenium enriched in $^{185}$Re may be used as a starting material.

Accordingly, in an embodiment of the second aspect, at least 65% of the rhenium atoms in the particles may be $^{187}$Re. For example, at least 80%, preferably at least 90%, mole preferably at least 95% and even more preferably at least 99%, such as about 99.6% of the rhenium atoms in the particles are $^{187}$Re.

Vice versa, at least 40%, in particular at least 60%, such as at least 80% of the rhenium atoms in the particles may be $^{185}$Re.

Further, details with respect to the rhenium compound, the composition of the particles, particle size distribution, etc. are as discussed above in the context of the process according to the first aspect of the present invention.

According to a third aspect of the present invention, there is provided an activated particle, wherein said particle is obtainable by the process according to the first aspect of the invention.

Further, according to a fourth aspect of the present invention there is provided a starting particle, wherein said particle is obtainable by the processes according to the second aspect of the invention.

According to a fifth aspect, the present invention provides a non-volatile and water-insoluble activated particle comprising a rhenium compound and $^{188}$Re atoms, wherein a ratio of $^{188}$W atoms to $^{188}$Re atoms in said activated particle is less than 50 ppm. In this context, the term "ratio" is used to refer to the quantitative relationship between $^{188}$W atoms and $^{188}$Re atoms, i.e. the number of $^{188}$W atoms contained in the particles per one million $^{188}$Re atoms. In a preferred embodiment, the non-volatile and water-insoluble activated particles are substantially free of $^{188}$W atoms.

According to an insight of the inventors, when eluting $^{188}$Re from $^{188}$W/$^{188}$Re generators during the conventional method, $^{188}$W impurities are basically unavoidable. Such $^{188}$W impurities, however, entail a significant risk in terms of radiation protection due to the comparably long half-life of $^{188}$W (about 70 days). Unfortunately, $^{188}$W impurities can only be detected after several half-lives of $^{188}$Re (i.e. several times the half-life of about 17 hours). This results in either loosing radioactivity during the time of waiting until the composition of the $^{188}$W/$^{188}$Re generator eluate can be determined or the use of material with an unknown degree of $^{188}$W impurities that may result in waste management problems.

In an embodiment of the activated particles according to the fifth aspect of the present invention, at least 65% of the rhenium atoms are $^{187}$Re and $^{188}$Re. In particular, at least 80%, preferably at least 90%, more preferably at least 95% and even more preferably at least 99%, such as about 99.6% of the rhenium atoms may be $^{187}$Re and $^{188}$Re.

According to a sixth aspect of the present invention, there is provided a non-volatile and water-insoluble activated particle comprising a rhenium compound and $^{186}$Re. Optionally at least 40%, in particular at least 60%, such as at least 80% of the rhenium atoms are $^{185}$Re and $^{186}$Re.

According to a specific embodiment of the fifth and sixth aspect, the particles have directly after activation an activity of 1-600 GBq per 10 mg rhenium, preferably an activity of 2-50 GBq per 10 mg rhenium. In this context, the term "directly after activation" as used herein means the radioactivity value as determined in a control sample within 10 minutes following activation in the neutron source, or as extrapolated to that time point.

The activation of the particles is desirably controlled to provide a defined activity for the intended use. For example, when the intended use is epidermal radionuclide therapy, it is desirable to apply to a skin region to be treated an activity within the range of from 25-400 MBq/cm$^2$, which translates to an exposition term between roughly 15 minutes to 4 hours. Accordingly, when it is intended to use the particles in epidermal radionuclide therapy, the activation is preferably controlled to provide an activity at the time of the treatment within the range of from 25-400 MBq per cm$^2$ of skin region to be treated, in particular within the range of from 50-150 MBq per cm$^2$ of skin region to be treated. As is understood by the skilled person, the activation takes into account the estimated time span between activation and actual use.

Based on the above considerations, the required activation time may be calculated. This calculation typically includes an estimated amount for the process loss and losses due to radioactive decays. The formula describing the radioactivity A produced by neutron activation is given by:

$$A = N^* \sigma^* \varphi^* [1 - 2^{\wedge}(-t_{irr}/T_{1/2})] \quad \text{(Formula V)}$$

Where $\varphi$ indicates the neutron flux in neutrons/cm$^2$/s, N is the amount of atoms of the irradiated isotope, a is the cross section of the irradiated isotope, $T_{1/2}$ is the half-life of the daughter isotope and $t_{irr}$ is the irradiation time, with $T_{1/2}$ and $t_{irr}$ being in the same time unit. N can be calculated from Formula (VI) with the mass m in g of the irradiated isotope and its atomic weight w in g/mol.

$$N = 6.022 * 10^{23} \text{ 1/mol} * m/w \quad \text{(Formula VI)}$$

According to a seventh aspect, the present invention provides a non-volatile and water-insoluble isolated starting particle comprising a rhenium compound, the particle having a particle size in the range of 1 nanometer to 100 micrometers. For example, the particles have an average particle size in the range of from 10 nanometers to 20 micrometers, from 20 nanometers to 10 micrometers, or from 50 nm to 5 micrometers.

According to a particular embodiment of the starting particle according to the seventh aspect, the rhenium compound of the particles may be derived from rhenium having an isotope distribution other than the natural isotope distribution. In particular, the rhenium compound of the particles may be derived from rhenium enriched in $^{187}$Re. According to such embodiment, at least 65% of the rhenium atoms may be $^{187}$Re. For example, at least 80%, preferably at least 90%, more preferably at least 95% and even more preferably at least 99%, such as about 99.6% of the rhenium atoms may be $^{187}$Re.

Vice versa, the rhenium compound of the particles according to the seventh aspect of the present invention may be derived from enriched in $^{185}$Re. According to such embodiment, at least 40%, in particular at least 60%, such as at least 80% of the rhenium atoms may be $^{185}$Re.

Further, the invention provides a specific embodiment, wherein the weight percentage of the rhenium compound in the particles according to one of the fifth, sixth or seventh aspect is at least 60%, preferably at least 70%, more preferably at least 75%, for example at least 80%.

As discussed already above in the context of the processes of the present invention, the particle of any of the fifth, sixth and seventh aspect further may comprise at least one additive such as polyvinylpyrrolidone (PVP), polyethylene glycol (PEG) and combinations thereof.

In particular, the particles may comprise 1 to 50 wt % polyvinylpyrrolidone (PVP) or polyethylene glycol (PEG), based on the weight of rhenium. In other words, the particles may comprise 0.01 to 0.5 mg PVP, such as 0.05 to 0.3 mg PVP per 1 mg of the rhenium compound.

Further as discussed already above in the context of the processes of the present invention, the rhenium compound of the particle of any of the fifth, sixth and seventh aspect may be selected from a rhenium sulfide, a rhenium oxide, and combinations thereof. In particular, the rhenium compound may be selected from dirhenium heptasulfide, rhenium disulfide, rhenium dioxide, rhenium trioxide, dirhenium heptaoxide, and combinations thereof. In particular, the particles may comprise dirhenium heptasulfide in an amount of at least 50 wt %, optionally in combination with other rhenium compounds.

According to an eighth aspect of the present invention, there is provided a plurality of particles according to any one of aspects three to seven.

According to a preferred embodiment, the particles have an average particle size in the range of from 1 nanometer to 100 micrometers. Further details with respect to average particle size and particle size distribution of the plurality of particles are as discussed above, in particular as discussed above in the context of the process according to the first aspect of the present invention.

According to a ninth aspect, the present invention provides a composition comprising a plurality of activated particles according to the eighth aspect and a carrier. Further details with respect to the carrier, matrix component of the carrier, particulate filler, and distribution of the plurality of activated particles in the carrier are as discussed above, in particular as discussed above in the context of the process according to the first aspect of the present invention.

In a preferred embodiment of the composition according to the invention, the average particle size of the activated particles is at most 1.000% of the average particle size of the particulate filler. For example, the average particle size of the activated particles may be at most 500%, or at most 250% of the average particle size of the particulate filler. Vice versa, the average particle size of the particles may be for example at least 0.1%, at least 1%, at least 10% or at least 25% of the average particle size of the particulate filler.

According to a tenth aspect, the present invention contemplates using the activated particles, and in particular the composition according to the present invention in radionuclide therapy. In particular, the present invention contemplates using the activated particles, and in particular the composition according to the present invention in epidermal radionuclide therapy. In the context of the present invention, the term "epidermal radionuclide therapy" refers to a special type of brachytherapy, i.e. radiotherapy where the radiation source is placed onto or adjacent to the outer skin at the area requiring treatment.

The activated particles or the composition, respectively, according to the present invention may be used in a method of treatment of a skin lesion, which might be a cancerous or non-cancerous skin lesion. Specific examples of skin lesions which may be treated with the activated particles or the composition according to the present invention include basal cell carcinoma (BCC), squamous cell carcinoma (SCC), actinic keratosis, keloid. Bowen's disease (Morbus Bowen), extramammary Paget's disease (Morbus Paget), Queyrat's disease (Morbus Queyrat), cutaneous lymphoma, lentigo maligna, and lentigo maligna melanoma.

According to a related eleventh aspect, the present invention contemplates using the activated particles, and in particular the composition according to the present invention in cosmetic applications. One cosmetic application presently contemplated in particular relates to removing or desaturating a tattoo in a skin region. Another cosmetic application presently contemplated in particular relates to treating scar tissue or removing scars. Accordingly, the present invention also provides a method comprising applying a plurality of activated particles or the composition according to the present invention to a skin region of a subject in order to desaturate a tattoo in a skin legion or treat scar tissue.

EXAMPLES

Example 1: Preparation of Activated Particles

Enriched metallic $^{187}$Re (Traces Sciences International Corp, Canada; 99.6% $^{187}$Re, 0.4% $^{185}$Re) is reacted with $H_2O_2$ under alkaline conditions. The resulting solution of $NH_4{}^{187}ReO_4$ (about 10 mg) is mixed with 2.5 g thioacetamide, 3 mg PVP and 1 milliliter concentrated HCl and heated at 90° C. for 30 minutes. The particles are precipitated by centrifugation and the precipitate is separated from other residuals of the chemical reaction, as well as components that did not react (e.g. thioacetamide). Starting particles comprising $^{187}Re_2S_7$ are thus obtained. The particle size distribution of the obtained particles is depicted in FIG. 1. Only a single peak corresponding to a unimodal particle size distribution is visible. Undesired elements and organic impurities from the synthesis are analyzed for acceptance of the batch.

The starting particles obtained as described above (about 10 mg, based on the weight of rhenium) are irradiated at a neutron flux of $10^{14}$ neutrons/cm$^2$/s for 1 hour. The irradiation produced a radioactivity of 9 GBq.

Example 2: Comparative Example

Carrier-free $^{188}$Re (as perrhenate) is obtained from a $^{188}W/^{188}Re$ generator by elution with saline. The solution (about 3 mg $NH_4{}^{188}ReO_4$ per 10 ml) is processed to $^{188}Re_2S_7$ by adding thioacetamide and concentrated HCl as well as heating (90° C. for 30 minutes). The particle size distribution is analyzed, of a sample which has been stored until the radioactivity had decayed sufficiently. The obtained distribution is shown in FIG. 2. At least two different peaks can be distinguished, suggesting an at least bimodal particle size distribution.

Specific embodiments of the present invention are indicated in the following clauses:
(1) A process of producing activated particles comprising $^{188}$Re and/or $^{186}$Re, comprising:
  a) providing non-volatile and water-insoluble starting particles comprising a rhenium compound,
  b) irradiating the particles with neutrons, wherein at least part of the $^{187}$Re atoms undergo a neutron capture to form $^{188}$Re and/or wherein at least part of the $^{185}$Re atoms undergo a neutron capture to form $^{186}$Re, thereby forming said activated particles.
(2) The process of clause 1, wherein the step of providing said starting particles comprises:

i) providing a rhenium solution,
ii) optionally, mixing the rhenium solution with at least one additive,
iii) reacting the rhenium solution with a precipitating agent, thereby forming said rhenium compound,
iv) precipitating said rhenium compound,
v) isolating particles comprising the precipitated rhenium compound,
vi) optionally, washing and/or filtering and/or drying said particles.
(3) The process of clause 2, wherein step i) comprises:
ia) providing metallic rhenium,
ib) reacting the metallic rhenium, thereby obtaining a perrhenate solution,
(4) The process of any of the preceding clauses, wherein the step of providing the starting particles comprises reacting metallic rhenium using peroxide in alkaline conditions, thereby obtaining a perrhenate solution.
(5) The process of any of the preceding clauses, wherein the step of providing the starting particles comprises mixing a rhenium solution with at least one additive, in particular wherein the additive is selected from polyvinylpyrrolidone (PVP), polyethylene glycol (PEG) and combinations thereof.
(6) The process of clause 5, comprising mixing said rhenium solution with 1 to 50 wt % polyvinylpyrrolidone (PVP) or polyethylene glycol (PEG), based on the weight of rhenium.
(7) The process of any of the preceding clauses, wherein the step of providing the starting particles further comprises determining the composition of the starting particles and/or the particle size distribution of the starting particles and/or the moisture content of the starting particles.
(8) The process of any of the preceding clauses, wherein at least 65% of the rhenium atoms in the particles are $^{187}$Re and $^{188}$Re.
(9) The process of any of the preceding clauses, wherein at least 80%, preferably at least 90%, more preferably at least 95% and even more preferably at least 99%, such as about 99.6% of the rhenium atoms in the particles are $^{187}$Re and $^{188}$Re.
(10) The process of any of clauses 1 to 7, wherein at least 40%, in particular at least 60%, such as at least 80% of the rhenium atoms in the particles are $^{185}$Re and $^{186}$Re.
(11) The process of any of the preceding clauses, wherein the weight percentage of the rhenium compound in the particles is at least 60%, preferably at least 70%, more preferably at least 75%, for example at least 80%.
(12) The process of any of the preceding clauses, wherein said rhenium compound is selected from a rhenium sulfide, a rhenium oxide, and combinations thereof.
(13) The process of any of the preceding clauses, wherein said particles have a unimodal particle size distribution.
(14) The process of any of the preceding clauses, wherein said particles have an average particle size in the range of from 1 nanometer to 100 micrometers.
(15) The process of any of the preceding clauses, wherein said particles have a particle size distribution D90 in the range of 10 to 1,000% of the average particle size.
(16) The process of any of the preceding clauses, wherein the starting particles are irradiated with thermal neutrons.
(17) The process of any of the preceding clauses, further comprising mixing the activated particles with a matrix component.
(18) The process of clause 17, wherein the activated particles are homogeneously dispersed in the matrix component.
(19) The process of clause 17 or 18, wherein the matrix component is a resinous matrix, preferably a water-based resinous matrix and more preferably a water-based paint, for example an acrylic paint.
(20) The process of any of clauses 17-19, wherein the matrix component comprises a particulate filler.
(21) The process of clause 20, wherein the particulate filler comprises at least one oxide, sulfide, carbonate, or a combination thereof, in particular wherein the filler comprises for example $TiO_2$, $Al_2O_3$, $SiO_2$ and/or $Fe_2O_3$.
(22) The process of clause 20 or 21, wherein the average particle size of the particles is at most 1,000% of the average particle size of the particulate filler.
(23) A process of producing non-volatile and water-insoluble starting particles comprising a rhenium compound, said particles having an average particle size of from 1 nanometer to 100 micrometers, the process comprising:
i) providing a rhenium solution,
ii) optionally, mixing the rhenium solution with at least one additive,
iii) reacting the rhenium solution with a precipitating agent, thereby forming said rhenium compound.
iv) precipitating said rhenium compound.
v) isolating particles comprising the precipitated rhenium compound,
vi) optionally, washing and/or filtering and/or drying said particles.
(24) The process of clause 23, wherein step i) comprises:
ia) providing metallic rhenium,
ib) reacting the metallic rhenium, thereby obtaining a perrhenate solution,
(25) The process of clause 23 or 24, wherein step i) comprises reacting metallic rhenium using peroxide in alkaline conditions, thereby obtaining a perrhenate solution.
(26) The process of any of clauses 23 to 25, wherein in step ii) the rhenium solution is mixed with at least one additive, in particular wherein the additive is selected from polyvinylpyrrolidone (PVP), polyethylene glycol (PEG) and combinations thereof.
(27) The process of clause 26, comprising mixing said rhenium solution with 1 to 50 wt % polyvinylpyrrolidone or polyethylene glycol (PEG), based on the weight of rhenium.
(28) The process of any of clauses 23 to 27, wherein the step of providing the starting particles further comprises determining the composition of the starting particles and/or the particle size distribution of the starting particles and/or the moisture content of the starting particles.
(29) The process of any of clauses 23 to 28, wherein at least 65% of the rhenium atoms in the particles are $^{187}$Re.
(30) The process of any of clauses 23 to 29, wherein at least 80%, preferably at least 90%, more preferably at least 95% and even more preferably at least 99%, such as about 99.6% of the rhenium atoms in the particles are $^{187}$Re.
(31) The process of any of clauses 23 to 28, wherein at least 40%, in particular at least 60%, such as at least 80% of the rhenium atoms in the particles are $^{185}$Re.
(32) The process of any of clauses 23 to 31, wherein the weight percentage of the rhenium compound in the particles is at least 60%, preferably at least 70%, more preferably at least 75%, for example at least 99.6%.
(33) The process of any of clauses 23 to 32, wherein said rhenium compound is selected from a rhenium sulfide, a rhenium oxide, and combinations thereof.

(34) The process of any of clauses 23 to 33, wherein said starting particles have a unimodal particle size distribution.
(35) The process of any of clauses 23 to 34, wherein said starting particles have a particle size distribution D90 in the range of 10 to 1,000% of the average particle size.
(36) An activated particle, wherein said particle is obtainable by the process according to any of clauses 1 to 22.
(37) A starting particle, wherein said particle is obtainable by the process according to any of clauses 23 to 34.
(38) A non-volatile and water-insoluble activated particle comprising a rhenium compound and $^{188}$Re atoms, wherein a ratio of $^{188}$W atoms to $^{188}$Re atoms in said activated particle is less than 50 ppm.
(39) The particle of clause 38, wherein at least 65% of the rhenium atoms are $^{187}$Re and $^{188}$Re.
(40) The particle of clause 38 or 39, wherein at least 80%, preferably at least 90%, more preferably at least 95% and even more preferably at least 99%, such as about 99.6% of the rhenium atoms are $^{187}$Re and $^{188}$Re.
(41) A non-volatile and water-insoluble activated particle comprising a rhenium compound and $^{186}$Re atoms, wherein optionally at least 40%, in particular at least 60%, such as at least 80% of the rhenium atoms are $^{185}$Re and $^{186}$Re.
(42) The particle of any of clauses 38 to 41, having directly after activation an activity of 1-600 GBq per 10 mg rhenium, preferably an activity of 2-50 GBq per 10 mg rhenium.
(43) A non-volatile and water-insoluble isolated starting particle comprising a rhenium compound, the particle having a particle size in the range of from 1 nanometer to 100 micrometers.
(44) The particle of clause 43, wherein at least 65% of the rhenium atoms are $^{187}$Re.
(45) The particle of clause 43 or 44, wherein at least 80%, preferably at least 90%, more preferably at least 95% and even more preferably at least 99%, such as about 99.6% of the rhenium atoms are $^{187}$Re.
(46) The particle of clause 43, wherein at least 40%, in particular at least 60%, such as at least 80% of the rhenium atoms are $^{185}$Re.
(47) The particle of any of clauses 38 to 46, wherein the weight percentage of the rhenium compound is at least 60%, preferably at least 70%, more preferably at least 75%, for example at least 80%.
(48) The particle of any of clauses 38 to 47, further comprising at least one additive, in particular wherein the additive is selected from polyvinylpyrrolidone (PVP), polyethylene glycol (PEG) and combinations thereof.
(49) The particle of clause 48, comprising 1 to 50 wt % polyvinylpyrrolidone (PVP) or polyethylene glycol (PEG), based on the weight of rhenium.
(50) The particle of any of clauses 38 to 49, wherein said rhenium compound is selected from a rhenium sulfide, a rhenium oxide, and combinations thereof.
(51) A plurality of particles of any one of clauses 36 to 50.
(52) The plurality of particles of clause 51, wherein the particles have a unimodal particle size distribution.
(53) The plurality of particles of clause 51 or 52, wherein the particles have an average particle size in the range of from 1 nanometer to 100 micrometers.
(54) The plurality of particles of any of clauses 51 to 53, wherein the particles have a particle size distribution D90 in the range of 10 to 1,000% of the average particle size.
(55) A composition comprising a plurality of activated particles of any of clauses 51 to 54 and a carrier.
(56) The composition of clause 55, wherein the carrier comprises a matrix component.
(57) The composition of clause 56, wherein the activated particles are homogeneously dispersed in the matrix component.
(58) The composition of clause 56 or 57, wherein the matrix component is a resinous matrix, preferably a water-based resinous matrix and more preferably a water-based paint, for example acrylic paint.
(59) The composition of any of clauses 55 to 58 comprising a particulate filler.
(60) The composition of clause 59, wherein the particulate filler comprises at least one oxide, sulfide, carbonate, or a combination thereof, in particular wherein the filler comprises for example $TiO_2$, $Al_2O_3$, $SiO_2$ and/or $Fe_2O_3$.
(61) The composition of clause 59 or 60, wherein the average particle size of the activated particles is at most 1,000% of the average particle size of the particulate filler.
(62) The composition of any of clauses 55 to 61 or the plurality of particles of any of claims 51-54 for use in radionuclide therapy.
(63) The composition or plurality of particles for use of clause 62 in epidermal radionuclide therapy.
(64) The composition or plurality particles for use of clause 62 or 63 in the treatment of a skin lesion, preferably wherein the skin lesion is a cancerous or non-cancerous lesion, in particular wherein the skin lesion is selected from the group consisting of a basal cell carcinoma (BCC), a squamous cell carcinoma (SCC), an actinic keratosis, a keloid, Bowen's disease, extramammary Paget's disease, Queyrat's disease, cutaneous lymphoma, lentigo maligna, lentigo maligna melanoma.
(65) A method of desaturating a tattoo in a skin region or removing scars comprising applying the composition of any of clauses 55 to 61 or the plurality of activated particles of any of clauses 51 to 54 to the skin region.

REFERENCES

[1] Eisemann. N., et al. "Non-Melanoma Skin Cancer Incidence and Impact of Skin Cancer Screening on Incidence." The Journal of Investigative Dermatology 134, no. 1 (January 2014): 43-50.
[2] Levell, N. J., et al. "Basal Cell Carcinoma Epidemiology in the UK: The Elephant in the Room." Clinical and Experimental Dermatology 38, no. 4 (June 2013): 367 69.
[3] Norval, M., et al. "The Incidence and Body Site of Skin Cancers in the Population Groups of South Africa." Photodermatology, Photoimmunology & Photomedicine 30, no. 5 (October 2014): 262-65.
[4] Rogers, H. W., et al. "Incidence Estimate of Nonmelanoma Skin Cancer in the United States, 2006." Archives of Dermatology 146, no. 3 (March 2010): 283-87.
[5] Haves, A. W., et al. "The Impact of Inoperable Advanced Basal Cell Carcinoma: The Economic, Physical, and Psychological Burden of the Disease." Journal of Drugs in Dermatology: JDD 12, no. 10 Suppl (October 2013): s151-53.
[6] Garcia, L., et al. "Basal Cell Carcinoma of the Nasolabial Fold: An Apparently 'Benign' Tumour That Often Needs Complex Surgery." Journal of the European Academy of Dermatology and Venereology: JEADV 20, no. 8 (September 2006): 926-30.
[7] Bichakjian, C. K., et al. "Basal Cell Skin Cancer." NCCN Clinical Practice Guidelines in Oncology. Version 1.2015. NCCN.org.

The invention claimed is:

1. A process of producing activated particles comprising $^{188}$Re and/or $^{186}$Re, comprising:
   a) providing non-volatile and water-insoluble starting particles comprising a rhenium sulfide, wherein at least 40% of the rhenium atoms are $^{185}$Re-atoms or at least 65% of the rhenium atoms are $^{187}$Re-atoms, the particles having a particle size in the range of from 1 nanometer to 20 micrometers,
   b) irradiating the particles with neutrons, wherein at least part of the $^{187}$Re-atoms undergo a neutron capture to form $^{188}$Re and/or wherein at least part of the $^{185}$Re-atoms undergo a neutron capture to form $^{186}$Re, thereby forming said activated particles.

2. The process of claim 1, further comprising mixing the activated particles with a matrix component.

3. A process of producing the non-volatile and water-insoluble starting particles of claim 1, the process comprising:
   i) providing a rhenium solution, wherein at least 40% of the rhenium atoms are $^{185}$Re-atoms or at least 65% of the rhenium atoms are $^{187}$Re-atoms,
   ii) optionally, mixing the rhenium solution with at least one additive,
   iii) reacting the rhenium solution with a precipitating agent, thereby forming said rhenium sulfide,
   iv) precipitating said rhenium sulfide,
   v) isolating particles comprising the precipitated rhenium sulfide,
   vi) optionally, washing and/or filtering and/or drying said particles.

4. A non-volatile and water-insoluble activated particle obtained by the process of claim 1, the particle comprising rhenium sulfide, wherein at least 40% of the rhenium atoms are $^{185}$Re-atoms and $^{186}$Re-atoms, the particle having a particle size in the range of from 1 nanometer to 20 micrometers.

5. The activated particle of claim 4, wherein at least 60% of the rhenium atoms are $^{185}$Re-atoms and $^{186}$Re-atoms.

6. A composition comprising a plurality of activated particles of claim 4 and a carrier.

7. A method of desaturating a tattoo in a skin region or of treating scar tissue in a skin region, the method comprising applying the composition of claim 6 to the skin region.

8. A method of desaturating a tattoo in a skin region or of treating scar tissue in a skin region, the method comprising applying a plurality of activated particles of claim 4 to the skin region.

9. A plurality of activated particles of claim 4 for use in radionuclide therapy.

10. A plurality of activated particles of claim 4 for use in the treatment of a skin lesion.

11. The plurality of activated particles of claim 10, wherein the skin lesion is a cancerous or non-cancerous lesion.

12. The plurality of activated particles of claim 11, wherein the skin lesion is selected from the group consisting of a basal cell carcinoma (BCC), a squamous cell carcinoma (SCC), an actinic keratosis, a keloid, Bowen's disease (Morbus Bowen), extramammary Paget's disease (Morbus Paget), Queyrat's disease (Morbus Queyrat), cutaneous lymphoma, lentigo maligna, lentigo maligna melanoma.

13. A non-volatile and water-insoluble activated particle obtained by the process of claim 1, said particle comprising rhenium sulfide, wherein at least 65% of the rhenium atoms are $^{187}$Re-atoms and $^{188}$Re-atoms, the particle having a particle size in the range of from 1 nanometer to 20 micrometers.

14. The activated particle of claim 13, wherein at least 80% of the rhenium atoms are $^{187}$Re-atoms and $^{188}$Re-atoms.

15. A composition comprising a plurality of activated particles of claim 13 and a carrier.

16. A plurality of activated particles of claim 13 for use in radionuclide therapy.

17. A plurality of activated particles of claim 13 for use in the treatment of a skin lesion.

18. The plurality of activated particles of claim 17, wherein the skin lesion is a cancerous or non-cancerous lesion.

19. The plurality of activated particles of claim 18, wherein the skin lesion is selected from the group consisting of a basal cell carcinoma (BCC), a squamous cell carcinoma (SCC), an actinic keratosis, a keloid, Bowen's disease (Morbus Bowen), extramammary Paget's disease (Morbus Paget), Queyrat's disease (Morbus Queyrat), cutaneous lymphoma, lentigo maligna, lentigo maligna melanoma.

20. A method of desaturating a tattoo in a skin region or of treating scar tissue in a skin region, the method comprising applying the composition of claim 15 to the skin region.

21. A method of desaturating a tattoo in a skin region or of treating scar tissue in a skin region, the method comprising applying a plurality of activated particles of claim 13 to the skin region.

* * * * *